United States Patent [19]

Ringrose et al.

[11] Patent Number: 5,698,450

[45] Date of Patent: Dec. 16, 1997

[54] METHOD FOR MEASURING ANTIGENS OR ANTIBODIES IN BIOLOGICAL FLUIDS

[76] Inventors: Anthony Ringrose, 124, Chemin de la Montagne, 1224 Chene-Bougeries; Rudolf Farkas, 38, Av. William Favre, 1207 Geneva; André Nicole, 17, chemin de la Gouille-Noire, 1244 Choulex; Jean-Louis Prost, 3, rue de l'Université, 1205 Geneva, all of Switzerland

[21] Appl. No.: 532,258

[22] Filed: Sep. 22, 1995

Related U.S. Application Data

[63] Continuation of Ser. No. 264,756, Jun. 23, 1994, abandoned, which is a continuation of Ser. No. 978,478, Nov. 18, 1992, abandoned, which is a division of Ser. No. 228,922, Aug. 15, 1988, abandoned.

[30] Foreign Application Priority Data

Oct. 14, 1986 [CH] Switzerland ............... 4096/86

[51] Int. Cl.⁶ ............... G01N 33/553; G01N 35/02
[52] U.S. Cl. ............... 436/526; 422/63; 422/64; 422/67; 422/82.05; 422/82.09; 422/68.1; 435/7.9; 435/7.92; 435/7.94; 435/287.1; 435/287.2; 435/288.7; 436/43; 436/47; 436/49; 436/50; 436/165; 436/518; 436/524; 436/536; 436/538; 436/541; 436/807; 436/809
[58] Field of Search ............... 422/63–65, 67, 422/68.1, 82.05, 82.09; 435/7.9, 7.92, 7.94, 287.1, 287.2, 288.7; 436/43, 47, 49, 50, 165, 518, 524, 526, 528, 531, 534, 536, 538, 541, 807, 809

[56] References Cited

U.S. PATENT DOCUMENTS

| | | | |
|---|---|---|---|
| 3,607,478 | 9/1971 | Hennings | 156/345 |
| 3,873,273 | 3/1975 | Moran | 356/246 |
| 3,951,608 | 4/1976 | Trod | 23/259 |
| 3,964,867 | 6/1976 | Berry | 356/246 |
| 4,058,367 | 11/1977 | Gilford | 364/416 |
| 4,130,395 | 12/1978 | Chryssanthou | 422/67 |
| 4,438,086 | 3/1984 | Forrest | 436/526 |

(List continued on next page.)

FOREIGN PATENT DOCUMENTS

| | | |
|---|---|---|
| 0087028 | 8/1983 | European Pat. Off. |
| 55-89753 | 7/1980 | Japan |
| 58-32362 | 2/1983 | Japan |
| 60-58235 | 4/1985 | Japan |
| 60-207058 | 10/1985 | Japan |
| 61-68562 | 4/1986 | Japan |
| 2005019 | 4/1979 | United Kingdom |

OTHER PUBLICATIONS

WO, A 83/00393 (American Hospital Supply Copr.) 3 Feb. 1983.
WO A, 83/01119 (Commonwealth Serum Laboratorie Commission) 31 Mar. 1983.

*Primary Examiner*—Christopher L. Chin
*Attorney, Agent, or Firm*—Cushman Darby & Cushman Intellectual Property Group of Pillsbury Madison & Sutro, LLP

[57] ABSTRACT

The invention relates to a method of measuring antigens or antibodies in biological fluids in appropriately designed reaction cells in an automated analytical apparatus. The method includes the steps of contacting, in the reaction cell, the biological fluid with antibodies specific for a desired analyte antigen, which antibodies are coated on magnetic particulate carrier, under conditions such that binding of the antibody to the desired analyte antigen occurs, and detecting the presence or absence of an immunocomplex formed between the antibody and the desired analyte antigen. The automated analytical apparatus includes a closed circuit transfer path having means for transferring cells around the entire transfer path, and a thermostating period for each analysis to be performed with the automated analytical apparatus. The transfer path includes a loading station, a reagent delivery station, a mixing and washing station, a separating station and a discharging station. A specific code is placed on each cell for identifying a kind of analysis to be effected with respect to that cell.

9 Claims, 6 Drawing Sheets

U.S. PATENT DOCUMENTS

| | | | |
|---|---|---|---|
| 4,540,549 | 9/1985 | Manabe | 422/64 |
| 4,634,575 | 1/1987 | Kawakami | 422/64 |
| 4,708,940 | 11/1987 | Yoshida et al. | 436/45 |
| 4,785,407 | 11/1988 | Sakagami | 422/64 |
| 4,793,973 | 12/1988 | Ringrose | 422/58 |
| 4,844,868 | 7/1989 | Rokugawa | 422/64 |
| 5,175,086 | 12/1992 | Takekawa et al. | 422/64 |

METHOD FOR MEASURING ANTIGENS OR ANTIBODIES IN BIOLOGICAL FLUIDS

This is a continuation of application Ser. No. 08/264,756, filed on Jun. 23, 1994, which was abandoned upon the filing hereof which was a Continuation of application Ser. No. 07/978,478 filed Nov. 18, 1992, now abandoned, which was a Division of application Ser. No. 07/228,922 filed Aug. 15, 1988, now abandoned.

The present invention concerns an automated analytical apparatus for measuring antigens or antibodies in biological fluids by the formation of specific antigen/antibody complex products. The complex product results from the addition of two or more complex-forming partners in a measuring cell, one of said partner reactants being optionally initially bound to magnetic particles. The apparatus comprises means for thermostatting the analytical cell during incubation of the content thereof, and a transfer device operating stepwise in a closed-circuit to displace the cells from a loading station toward a discharge station through intermediate stations, the intermediate stations comprising pipet reagent delivery stations, blending stations, washing and separation stations, all of these being involved in carrying out a plurality of specific analyses for which the apparatus is designed.

Apparatuses of a type capable of effecting various kinds of biological analyses on different liquids have already been reported. Since every kind of analysis requires the use of at least one specific reagent, it is generally inconvenient to store several of these reagents in the apparatus itself. It is preferable to have the reagents closely associated with each respective analytical cell; hence, when carrying out one specific kind of analysis, one has to use a specific reaction cell containing a specific analytical reagent associated with that cell. In some cases, the reagents are in the form of coatings on the cell walls. In other cases, reagents specific of analytes are deposited on beads and the coated beads react with the analyte after introduction into the cell. The advantage of these techniques is to avoid separation steps by centrifugation; however, a disadvantage is the relatively small area of the available reagent coated surfaces, meaning decreased sensitivity.

Other embodiments exist in which the reagents are incorporated into very small particles such as latex particles, i.e. coated with antigen or antibody reactants. In these embodiments where antigen/antibody complexes are formed, one measures the percent of particles harboring said complexes relative to the total number of particles. Thus, a technique of this kind requires somewhere a separation step by centrifugation. For this, one can either gather on a single rotor all cells subjected to the same reaction conditions or, otherwise, in the case of a plurality of cells subjected to different conditions, the latter must be transferred at some stage from a reaction station to the centrifugation rotor. Consequently, the first case only enables the performance of reactions of the same kind as, with different kinds of reactions, the incubation times would be different, and in the second case, the transfer step will require using mechanisms of sophisticated complexity.

It has also been proposed to immobilize immunoreactants on magnetic particles usually by means of intermediate unspecific coupling agents; hence the separation of the particles after formation of an antigen/antibody complex on the surface of the particle can be achieved without centrifugation. After separation, consecutive to applying a magnetic field, the liquid is removed from the cell, the latter is rinsed and a new reagent is introduced into contact with the particles which reacts with an enzyme label attached to the immobilized immunoreactant and generates a color signal which is then measured.

The object of the present invention is an automated apparatus for measuring antigens or antibodies in a biological fluid and capable of carrying out several types of analyses simultaneously, i.e. with this apparatus it is unnecessary to gather together several cells subjected to the same analysis on a common rotating deck and to wait until the analysis is terminated before undertaking analysis of a different type by using another series of cells.

Thus, an analytical apparatus suitable for the automated measuring of antigens or antibodies in a biological liquid is defined in the annexed claims.

This apparatus of the invention has many advantages. It is very versatile and can simultaneously effect a large number of tests of different kinds. For this, each cell is worked independently of other cells located before or after it. The magnetic particles used for reagent immobilization are very small and they have an extensive specific area for building antigen/antibody immunocomplexes which allows excellent sensitivity. No centrifugation step is necessary to effect separation which is performed by simply using a magnet. This separation can be controllably effected at a desired time which enables the incubation periods to vary in function to different analytes and reactants. No radioactive markers are necessary and problems of protection from radiation can be ignored.

Under practical conditions, the present apparatus is conceptually simple, easy to use and, because of its flexibility, it is adapted to hospital laboratory work as well as to medical home practice. Indeed, during daily consultations, a doctor may wish to measure at short intervals various fluids involving immunoreactions of different kinds. In contrast to what normally happens in laboratories, it is not readily convenient for him to collect during a day a number of analytical samples of the same kind sufficient to fully load the rack of an apparatus only designed to this kind of analyte. On the contrary, with the apparatus of the invention, a doctor may for instance collect daily many samples of different fluids and subject them to analyses practically simultaneously, each cell being worked independently according to the kind of analysis desired.

The annexed drawing illustrates for the purpose of exemplification an embodiment of the automated analytical apparatus of the invention.

In the following description, the term "biological liquid" defines any fluid, suspension, solution or emulsion containing a biological substance in a biological medium.

Figure 2:
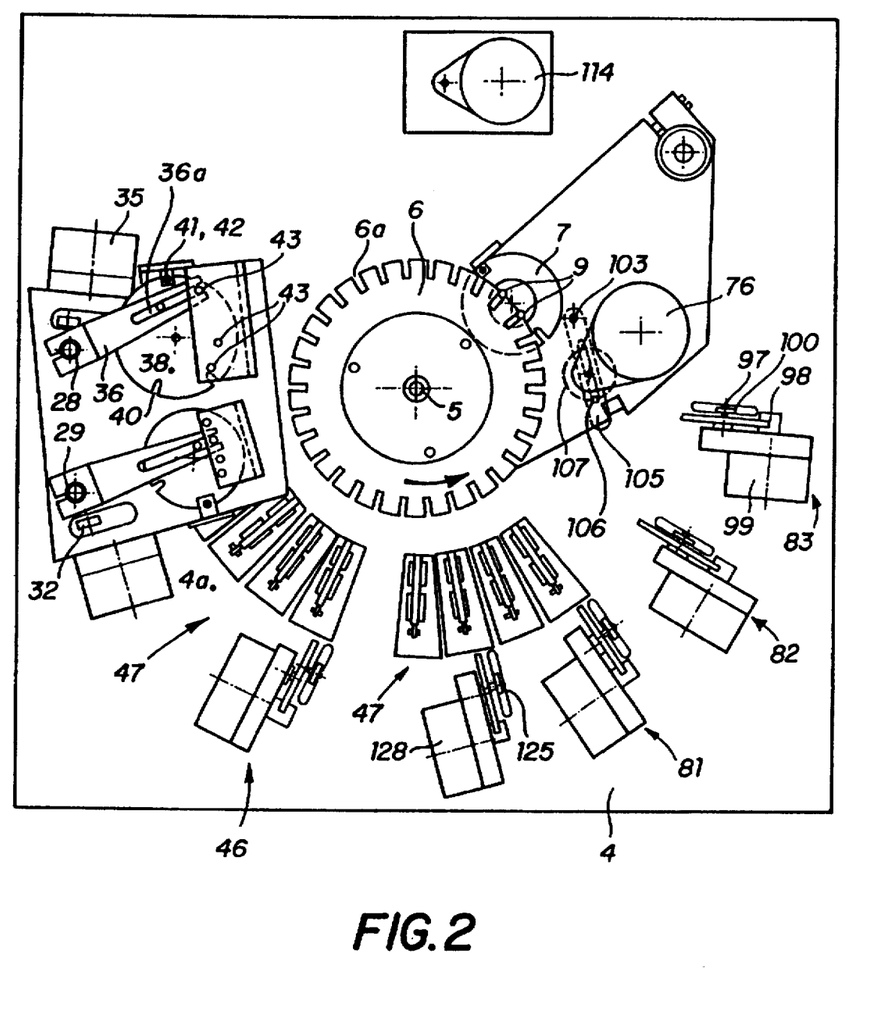
FIG. 2 is a view of the underside of the apparatus.
Figure 7:
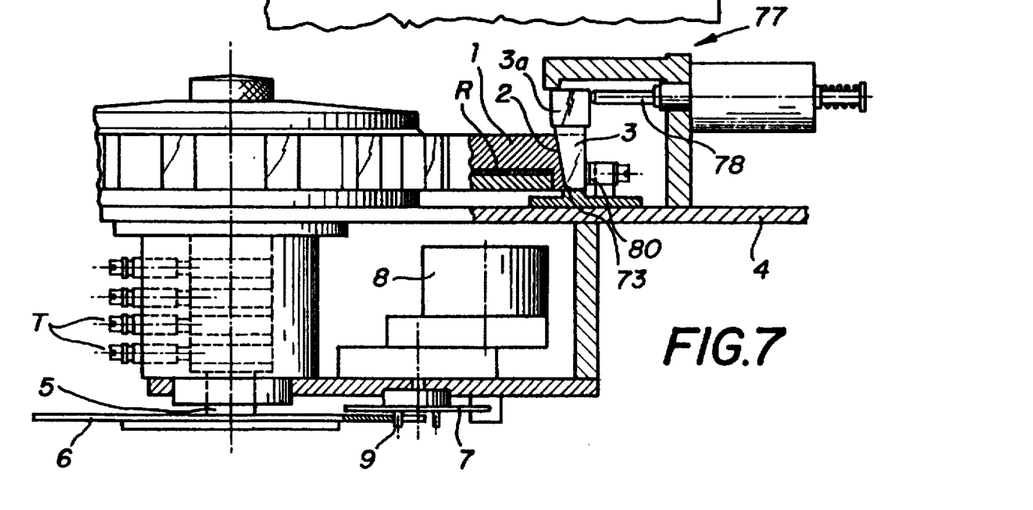
FIG. 7 is a third radial cross-sectional view of FIG. 1.

The present analytical apparatus comprises a transfer disk-shaped rack 1 provided with peripheral radial housing recesses 2, evenly spaced, for holding the reaction cells 3 of the samples to be analyzed. This transfer disk 1 is rotatably mounted on a frame 4 by means of a shaft 5 which crosses this frame 4 and which bears, on underside thereof, a radially slotted wheel 6, 6a (FIG. 2, 7). A driving gear 7 fastened to a step-by-step motor 8 carries two pegs 9 whose radial separation matches with that of two consecutive radial slots in wheel 6. The axle of this driving pinnion 7 coincides with the edge of the radially slotted wheel 6, so after each half-turn of the driving pinnion 7, the pegs 9 re-engage with two adjacent radial slots 6a, the wheel 6 being driven one step forward. Obviously, each displacement step of the wheel 6 corresponds to one of the advancing steps of the radial recesses 2 of the transfer rack 1.

The transfer disk-shaped rack 1 is made of a relatively thick aluminium plate, but this thickness is slightly lower than the portion of the cells 3 which is below two side containers 3a coupled to two respective reaction compartments 3b whose bottoms rest on the surface of the transfer disk 1 on both sides of the radial recess 2. The shape of these radial recesses closely matches with that of the portion of the cells resting therein, so that a very tight contact between the walls of the radial recesses 2 and the cell walls is ensured.

Electrical heating elements R (FIG. 4–7) are embedded in the body of aluminium of the transfer disk 1 and are under control from a thermostat element T adapted to maintain the temperature of the transfer disk 1 to a desired value which depends on the incubation temperature required for reacting the analyte samples in the cells 3 with the respective corresponding reagents.

Figure 1:
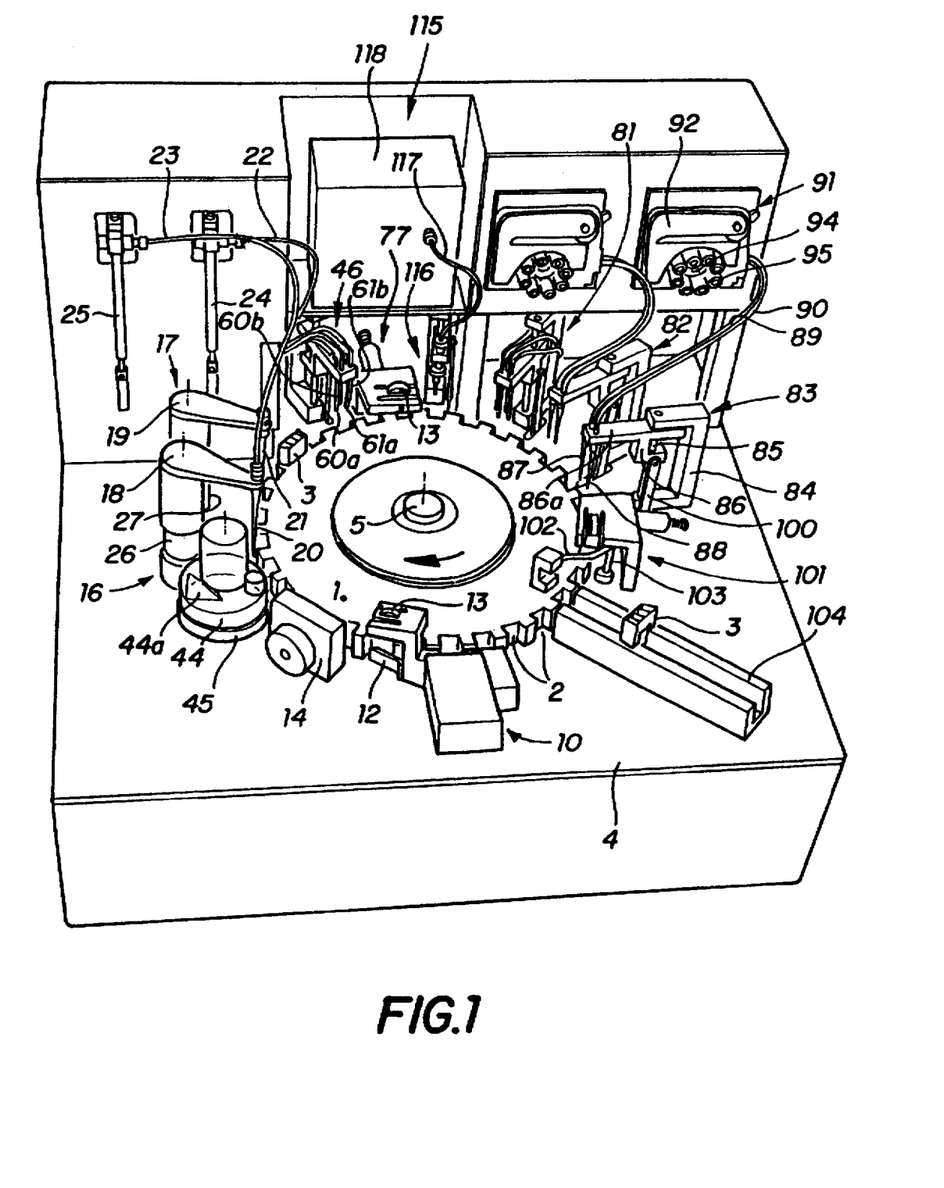
FIG. 1 is a view in perspective of the apparatus as a whole.
Figure 3:
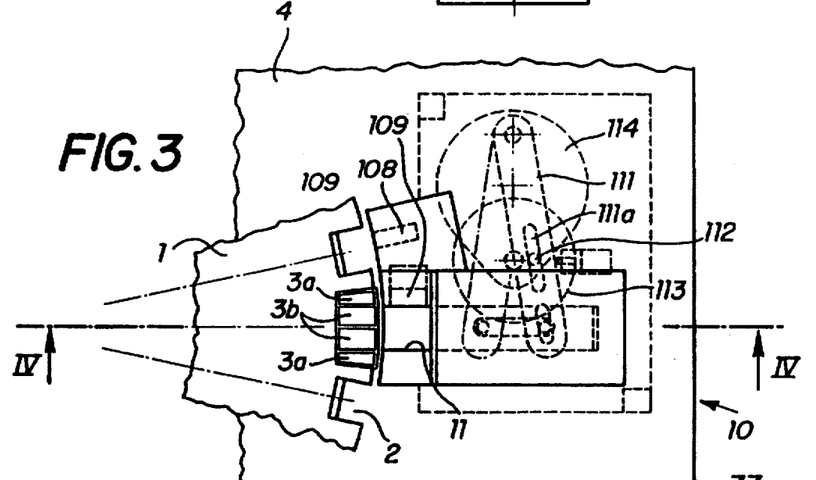
FIG. 3 is an enlarged plan view of part of FIG. 1.
Figure 4:
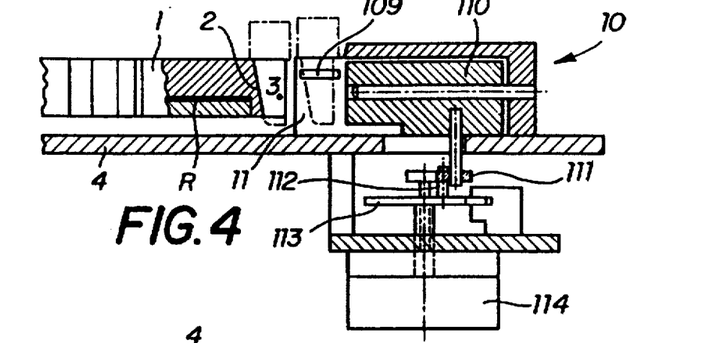
FIG. 4 is a cross-section along line IV—IV of FIG. 3.

Several working stations are distributed over frame 4 around the transfer rack 1. The first station is a loading unit 10 in which the cells 3 are set up in the radial recesses 2 of the transfer rack 1 (FIG. 1, 3 and 4). This unit 10 comprises an approaching-ramp 11 for the cells 3 which opens opposite to one of the radial recesses 2. This unit also carries a spring-blade 12 and a roller journalled on a horizontal shaft. This blade 12 and the roller 13 are made of a resilient material and are designed to press, respectively sidewise and topwise, the loaded cells 3 on the disk 1 to provide a contact as tight as possible of the walls of the radial recess 2 and the cell walls to ensure appropriate thermostatting of the samples within the cells and consequent reproducible incubation conditions.

The side wall of each cell 3 which faces the outside of the transfer disk 1 carries an identification sign coded in relation with the kind of analysis to be carried out. The coding is preferably digital and comprises a series of successively spaced bars of varying thickness which can be probed by a special sensor constituted by a high sensitivity reflexion detector from Hewlett-Packard. This sensor corresponds to the second working station which is connected to the input of control unit 15 illustrated by the block-diagram of FIG. 12 which will be described hereafter. The two following working stations are represented by two pipetting stations 16 and 17, each having a jig 18 and 19, respectively. An arm of each jig 18 and 19 bears at the free end thereof a hollow pointed dropper 20 and 21, respectively connected by flexible hoses 22 and 23, respectively to two calibrated pipettes 24 and 25, respectively constituted by calibrated tubes and pistons.

The vertical portion of each jig 18, 19 (FIG. 2, 5) comprises a tubular section 26, 27 respectively, fastened between frame 4 and an auxiliary fixture 4a, this section 26 containing a movable slidingly mounted tubular part 28, 29 respectively, whose upper end is provided with the jig's arm 18, 19 respectively.

Figures 5, 6:
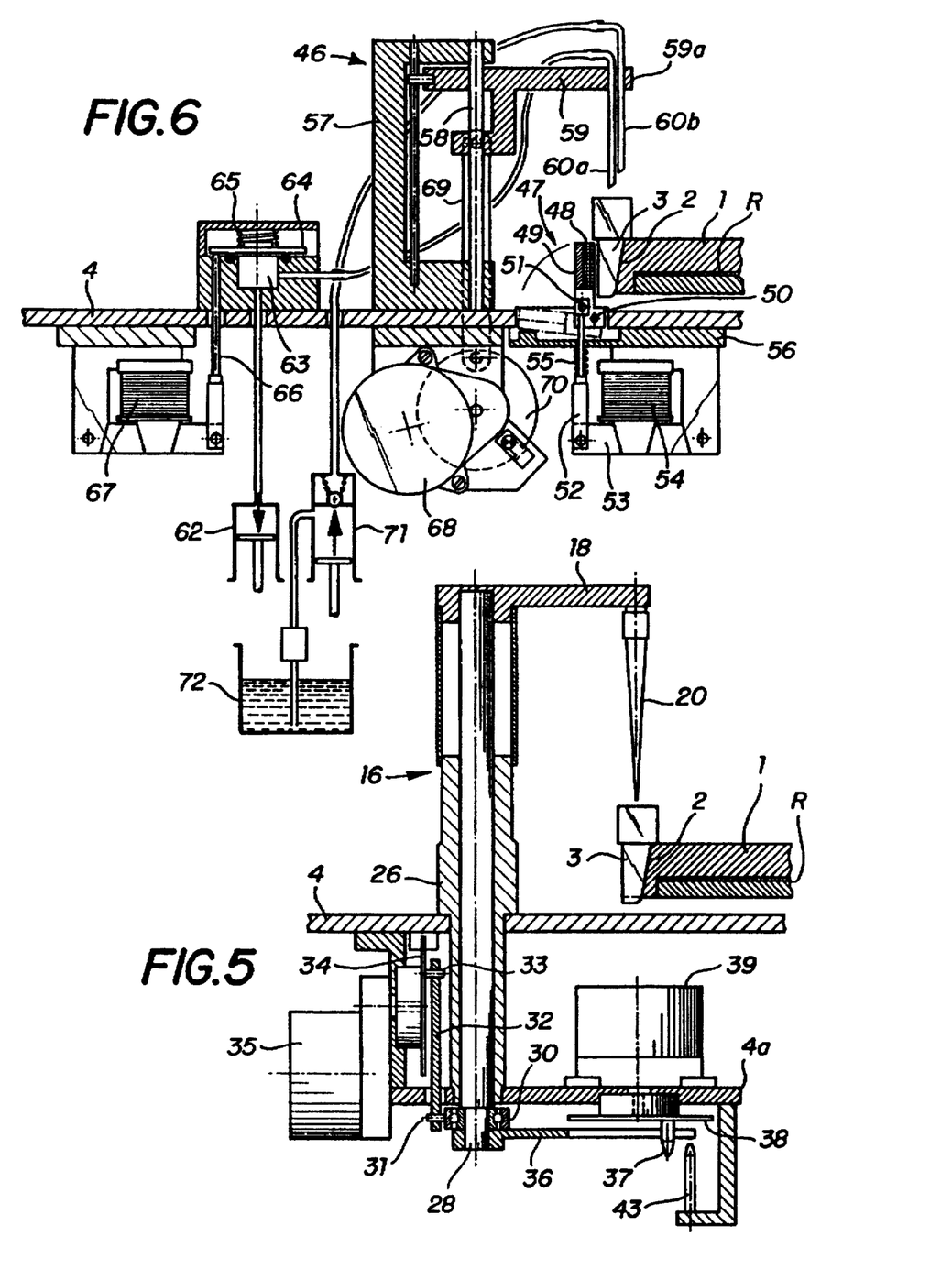
FIG. 5 is a first radial cross-sectional view of FIG. 1.
FIG. 6 is a second radial cross-sectional view of FIG. 1.

Since the driving mechanisms of both jigs are the same, only that of jig 18 is illustrated in FIG. 5 and is described in more detail hereafter in this disclosure.

The lower end of the movable tubular part 28 protrudes beyond the under-side of the auxiliary fixture 4a. This end is provided with a ball-bearing 30 whose outside ring comprises a lug 31 engaging in a rod 32 whose other end is in mesh with another lug 33 fastened crankwise to a disk 34 itself integral with a driving shaft of a synchronous motor 35 attached to the auxiliary fixture. This lower end of the movable tubular part 28 further carries an arm 36 which engages, through a slit 36a, with a pin 37 fastened to a disk 38 fixed to the driving shaff of a synchronous motor 39. This disk 38 (FIG. 2) is provided with peripheral radial slits 40 which move in front of a light source 41 facing a photodetector 42. By means of these slits, the angular position of disk 38 can be checked as a function of the desired angular position of the arm 36. The cut 36a which opens at the free end of the latter also engages with cylindrical guiding rods 43 fastened to the auxiliary fixture 4a in each of the angular position to be occupied by arm 36.

First pipetting point 16 transfers a suspension of magnetic particles in association with an antibody contained in a reservoir 44 (FIG. 1) mounted on a oscillating 45 alternatively driven into opposite directions around a vertical axis. Reservoir 44 is constant-level. A double ramp 44a protrudes from the bottom to promote agitation of the suspension in conjunction with the oscillations of the support 45.

The two liquid delivery stations 16 and 17 are followed by a first washing station 46 (FIG. 6) and, before this and coupled therewith, 4 identical magnetic separation devices 47 (FIG. 2 and 6) each located opposite to the periphery of the transfer disk 1 and angularly separated from each other by a distance corresponding to a step between two radial recesses 2. As all these magnetic separation devices are identical, only one of them is described herein. This device 47 comprises a permanent magnet 48 fastened to an oscillating carrier 49 journalled about a horizontal shaft 50 oriented in a tangent direction relative to the transfer disk 1. A connecting pin 51 is fastened, in parallel to shaft 50, to the oscillating carrier 49 and crosses one end of a push-rod 52 whose other end is hinged to a movable armature 53 of an elecromagnet 54. The push-rod 52 is surrounded by a compression return spring 55 compressed between this push-rod and a small plate 56 which links the device 47 to the framework 4. The reason for the existence of four magnetic separation stations, of which three are ahead of the washing station, is to provide a time sufficient for allowing all the magnetic particles to gather on the wall 3b of the reaction cells 3, this wall being adjacent to the permanent magnets 48 when the latter are brought very close to these walls by the rocking motion of the oscillating carrier 49, under the action of the electro-magnet 54 which operates the push-rod 52 through the action of the movable armature 53 and against the force of the return spring 55.

The first washing station 46 comprises a C-shaped bracket 57 of which one of the parallel arms is fastened to the frame 4. A slide guiding member 58 is located between the two arms of the C-bracket and guides a slide 59 provided with a side-arm 59a carrying at the end two pairs of hoses 60a and 60b (the only one represented on FIG. 6), 61 and 61b respectively (FIG. 1), each pair being disposed above one of the two reaction compartments 3b of each cell 3 when positioned at the wash station 46. The slide is connected to a synchronous driving motor 68 by means of a rod 69 of which one end is hinged to the slide 59 and the other end is eccentrically coupled to a disk 70 fastened to the driving shaft of the motor 68.

One of the hoses 60a, 61a in each pair is connected to a suction source 62 by means of a spout 63 controlled by a valve 64 elastically pressed against the seat of the spout 63 by a spring 65. A push-rod 66 coupled to a movable armature of an electromagnet 67 is arranged under the valve 64 to draw the valve from the seat of the spout 63 against the push of the spring 65, when the sucking action in reaction-compartments 3b is to be interrupted.

The other hoses 60b, 61b of each pair are connected to the outlet of a piston-pump 71 whose inlet is connected to a rinsing liquid reservoir 72.

The electromagnet 67 which actuates the push-rod 66 which drives the valve 64 is in synchronous relation with a synchronous driving motor (not represented) which actuates the piston of pump 71 to close the valve of the spout 63 for sucking through hoses 60a, 61a the liquids in each of reaction compartments 3b during the admission stroke of the piston of the pump 71, and during the escape stroke of the piston pump 71, to open this valve of spout 63 and thus to introduce a portion of rinsing liquid into each reaction compartments 3b through hoses 60b, 61b.

Figure 8:
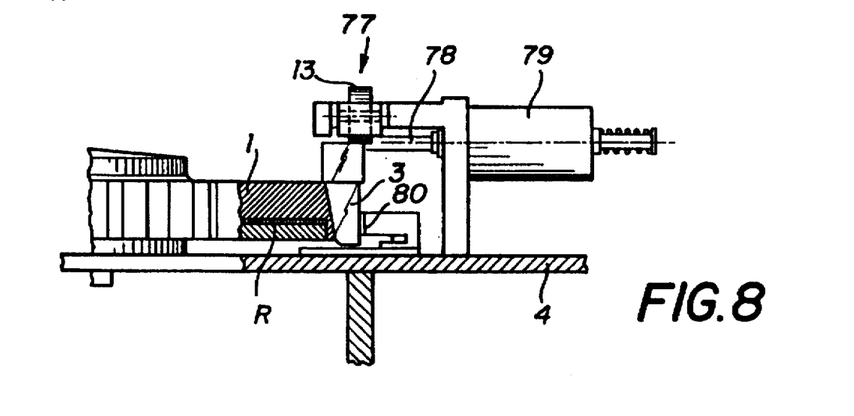
FIG. 8 is a fourth radial cross-sectional view of FIG. 1.

The first washing station 46 is followed by a first mixing station 77 comprising a rod 78 (FIG. 7, 8) integrally fastened to an electromagnet 79 which provides thereto a longitudinal oscillating motion. An incline 73 fastened to frame 4 enables the cell 3 to be slightly lifted during the mixing operation. This rod 78 is oriented in facing relation to with the portion of cell 3 located above the transfer disk 1, so its longitudinal displacement toward the disk center rocks the cell 3 around the upper plane of said disk 1. A return spring 80 maintains the lower part of the cell 3 against the wall of the radial recess 2 in which the cell 3 is positioned, so when the electromagnet 79 is no longer energized, the lower part of the cell 3 is pushed back against the wall of the radial recess 2, this succession of moves being at a frequency sufficient to agitate the contents of the cell. To improve the mixing efficiency, a small weight, for instance in this example a bead, is initially introduced in each of the reaction compartments 3b of this cell 3. Adjacent to the mixing station 77, is a roller 13 of the loading station 10; the blade 12 for providing a lateral pressure is not visible but, nevertheless, it exists on the apparatus.

The mixing station 77 is followed by four additional magnetic separation stations 47, the fourth of which is coupled to a second washing station 81 identical to the first washing station 46. The only difference between these two washing stations 46 and 81 is functional in nature. Hence the second washing station will not be further discussed here. Yet, although in the case of the first washing station 46, the washing cycle terminates with the dispensing of a washing liquid portion in each reaction compartment 3b, in the second washing station 81, the cycle terminates by removing by aspiration the liquid from these compartments 3b, so the cells 3 reach the next station with the magnetic particles carrying the bound antigens to be analyzed.

The two following stations 82 and 83 are for the stages of pipet dispensing a liquid substrate and for subsequently adding a reagent to stop the reaction of the enzyme marker bound to the solid phase of the metallic particles with the substrate, respectively.

The two pipetting stations 82, 83 (FIG. 1) are identical, so only one needs to be described in more detail. As for the washing stations 46 and 81, these pipetting stations each comprises a C-shaped supporting bracket 84 whose lower horizontal portion is fastened to frame 4. A slide guiding member 85 is located between the two parallel portions of bracket 84 to guide a slide 86 provided with a side arm 86a which carries at the end two hollow points 87, 88, which are connected by two flexible hoses 89 and 90, respectively, to a double channel peristaltic pump 91. In this Example, the pump is a high precision model manufactured by ISMATEC SA, Zurich, model "MINI-S-8".

This pump comprises a semi-circular base 92 against which lie the two flexible hoses 89, 90 which extend to a reservoir (not represented) of the product to be dispensed. A disk is rotatably mounted in the center of the semi-circular base 92 and is bolted to the driving shaft 94 of a motor (not represented). This disk carries, peripherically mounted, a series of cylinders 95 whose longitudinal axes are parallel to the rotation shaft 94 of the disk. The diameter of these cylinders is selected for allowing between them and the semi-circular base 92 a space amounting to twice the wall thickness of the flexible hoses 89, 90 i.e. to the thickness when the two hoses are pinched. When they turn around the rotation shaft 94, the cylinders 95 squeeze the flexible hoses 89, 90 at regular intervals which means catching a volume increment of liquid therebetween and driving away this volume as the rotation of the cylinders 95 continues. The angular displacement selected for the disk carrying the cylinders 95 determines the number of pumped volume increments and, as a consequence, the volume of the dispensed liquid.

The slide 86 is connected to an eccentric 97 (FIG. 2) of a driving plate clamped to a shaft of a synchronous motor 99 through a rod 100.

A second mixing station 101, (FIG. 1) identical to the mixing station 77 is placed after the pipetting station 83. An arm 102 is integral with a vertical shaft 103 oscillatingly mounted on frame 4 and switches the cells to a discharge ramp 104. The lower end of the vertical shaft 103 carries a horizontal arm 105 (FIG. 2) provided with a longitudinal groove which engages with an eccentric 106 integral with a driving plate 107 clamped on the shaft of a synchronous motor 76.

A photo-electric cell 108 acting as a presence detector (FIG. 3) precedes the loading unit 10 and is positioned opposite to the recess 2 which is one step before the recess 2 located opposite to the access-ramp 11. There is a second presence detector photo-cell in the access ramp 11. A loading push-rod 110 (FIG. 3 and 4) is slidably mounted on the loading unit 10 in the direction of extension of ramp 11. This push-rod 110 is fastened to an arm 111 extending sidewise, provided with a longitudinal groove in engagement with an eccentric 112 protruding from a rotating sheave fastened on the shaft of a synchronous motor 114.

A last station, constituted by a measuring unit 115 is positioned somewhere around the transfer rack 1. Since the reaction cells are programmed individually and that some may have to rotate with the transfer rack 1a number of revolutions different from others, the measuring station 115, which constitutes the last working station, can be anywhere around the transfer rack 1. In this example, one position was free between pipets 24 and 25 and peristaltic pumps 91, and it was chosen for practical reasons.

Figure 9:
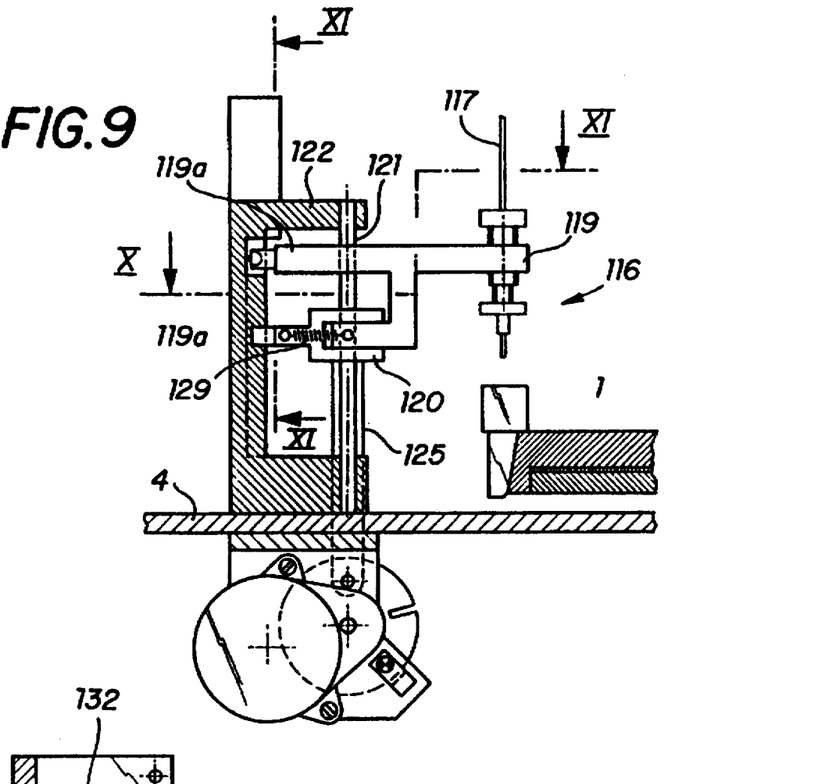
FIG. 9 is a fifth radial cross-sectional view of FIG. 1.

This measuring station 115 (FIG. 9, 10 and 11) comprises a pipet device 116 connected by means of a flexible hose 117 to a photometer, a commercial appliance from the Vital-Scientific Company (the Netherlands), type I.S.P. which is coupled to a pipetting contrivance to transfer the liquid to be analyzed into the measuring cuvette of this photometer.

Figure 10:
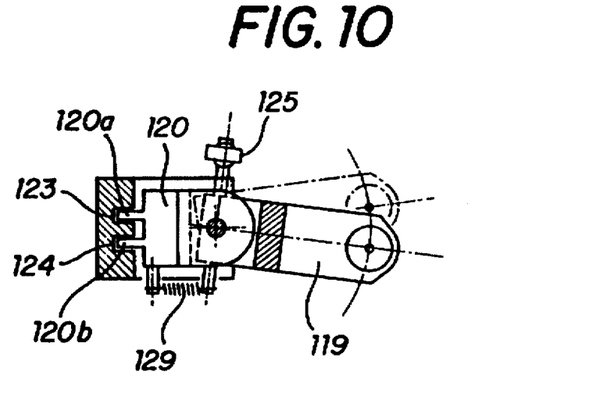
FIG. 10 is a cross-section along line X—X of FIG. 9.
Figure 11:
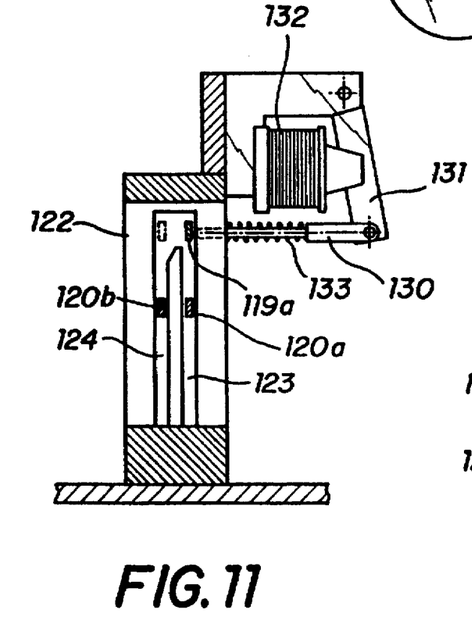
FIG. 11 is a cross-section along line XI—XI of FIG. 10.

The flexible hose 117 for drawing off the liquid is carried by an arm 119, journalled about a vertical shaft on a slide rod 120 mounted in a vertical slide guide 121 fastened to a C-shaped bracket 122 mounted on the frame 4. The arm 119 has a branch 119a whose end is in mesh with one or the other of grooves 123, 124 provided in the internal face of the vertical portion of the C-bracket 122. As shown in FIG. 10, the slide-rod 120 carries two fingers 120a, 120b in mesh with the two grooves 123, 124, respectively. FIG. 11 shows that these two grooves 123, 124 communicate with each other at their upper ends.

FIG. 10 shows that the connecting arm 119 is further coupled to a rod 125 by means of a knee-joint which gives this rod a certain degree of freedom relative to the angular displacement of the arm 119 whose amplitude can be estimated from the positions sketched in solid and interrupted lines. This arm is normally in a return position sketched in solid lines by means of a return spring 129 an end of which is bound to the arm and the other end of which is fastened to the slide rod. This rod 125 crosses frame 4 to come to engage next with an excentric 126 of a driving sheave fastened to the shaft of a driving motor 128 (FIG. 2).

A rod 130 is slidingly mounted in a side wall of the C-bracket 122 which defines the portion where the two grooves 123, 124 unite. This rod 130 is coupled to a movable armature 131 of an electromagnet 132 and drawn back by a return spring 133.

Figure 12:
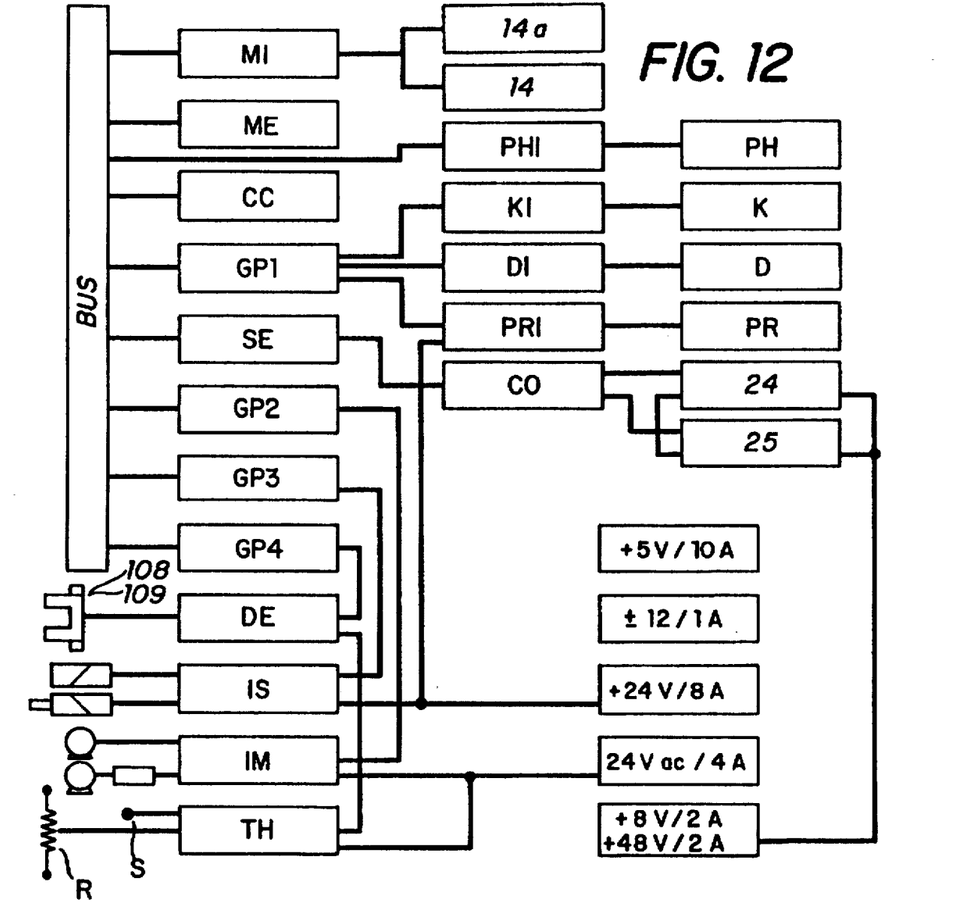
FIG. 12 is a block-diagram of the control system of the apparatus.

The block-diagram of FIG. 12 concerns an electronic circuit for controlling the analytical apparatus described above.

This block-diagram comprises two sets of circuit boards, one set comprising standard boards connected to a Bus bar and the other set comprising specific boards acting as interfaces between the controlling and actuating components of the apparatus and the remaining electronic processing circuits.

The heart of the circuit is a microprocessor board MI of the GESPAC Company, Geneva, reference GES SBS-4, comprising parallel and series input and outputs; the inputs are connected to the bar-code detector of each reaction cell 3 which is positioned opposite to the transfer disk 1. A second bar reading probe 14a is intented to supply the microprocessor with corrective and calibrating data according to the instructions provided by the manufacturer of each lot of cells loaded with specific reagents. Indeed, the reagents stored in the side reservoirs 3a of the cells can slightly vary from run to run. Depending on the characteristic of a lot, the manufacturer indicates as a bar code on the package the corrective and calibrating factors. The operator can then manually introduce the factors into the microprocessor memory by means of probe 14a.

Another standard board is an extension of the memory ME which supplements the memory of the microprocessor board when the amount of data exceeds the capacity of this memory. This board is wired to accept read-only memories (ROM) and random access memories (RAM), the latter being coupled to a battery in case of main power failure.

The battery powered board CC indicates the time and the date.

A general purpose input-output board GPI operates as an input and as an output element in connection with the operator's interfaces, i.e. key-board, display, printer.

An input-output board is series connected by a line RS-232C to an appliance CO for controlling the pipets.

Three general purpose input-output boards GP2, GP3, GP4 are used as follows: GP4 is programmed to operate as an input for the signals from a board DE working as an interface for the optical detectors 108 and 109 and for a thermostatting board TH coupled to a heating resistor R of the transfer rack 1 and to a gauge S to measure the temperature of this transfer rack 1. GP2 and GP3 are programmed to operate as output in interfaces for the interface boards IM an IS which control the several motors which drive the various components and the electromagnets of the magnetic separation and mixing station. All the boards connected to the BUS bar are available from the Company GESPAC, Geneva; the identifying reference numbers are: MEM-3 for memory ME; T1M-1A for board CC; P1A-2W for board GP1; S10-IE for board SE; P1A-2W for boards GP2, GP3, GP4.

Regarding the specific boards which constitute the interfaces between the various working components of the apparatus and the standard boards, it is noted that board DE is coupled with opto-electronic detectors which essentially operate by transmission or reflexion, and with the terminals of the thermostatting components. This board comprises input filters on the connecting lines with board GP4 (time constant 1 ms)

The board IM allows passing a low level digital signal, achieved by an electronic switch and with an AC voltage of 24V, to drive the synchronous motors.

The board IS allows transmitting a low level high power digital signal by a control stage. The full power is applied for a short while (0,3 sec) for driving mechanical parts, thereafter the working voltage is limited to about 20% of the nominal voltage to prevent overheating.

The thermostatting board provides proportional control, by means of a thermistor as dectector and a modulated power control acting on the pulse width. The control of the state of the board is achieved with two, lines according to the following scheme.

00: unconnected/open thermistor
01: too low temperature
10: too high temperature
11: correct temperature The latter is stabilized at 37°±0.2° C. If the thermistor is defective (state 00) the heating power is automatically interrupted.

For the BUS connecting bar and the boards connected thereto, different models from several manufacturers can be selected, i.e. STD-BUS (PROLOG), G-64 Bus (GESPAC), Eurobus (PEP).

Of course the whole of the circuits discussed here could be developped in the form of a specific microprocessor circuit board.

Components PH, K, D and PR concern the designation of, respectively, the measure photometer, the control keyboard, the display outfit and the printer which are conventional and not specifically described or illustrated within the present disclosure. Elements PHI, KI, DI, PRI represent the respective interface circuits for these components.

In the present embodiment, the transfer disk or rack 1 comprises thirty radial recesses 2 and can therefore accomodate 30 cells simultaneously. The time interval of two successive steps of the transfer disk 1 is 15 sec, so one revolution of the disk lasts 30×15 sec.=7.5 min. This 7.5 min. period does not correspond to the time of analysis of one sample but constitutes the basic incremental period to be used in all analyses carried out by the apparatus; in this connection, it is to be remembered that each cell 3 can remain on disk 1 the full time necessary to achieve the incubation of the analytical sample to be tested; this will be detailed hereafter.

When the apparatus is started, an angular reference mark on the transfer disk 1 is identified, i.e. the computing and controlling circuits establish the initial position of one radial recess 2 and, consequently, the position of No 1 cell 3, which permits to successively order by numbers up to 30 the remaining recesses and corresponding cells, thus allowing to subsequently determine at any moment the numbering of any cell 3 in a given angular position.

When a cell becomes positioned on the access incline 11, it is detected by the detector probe 109 which transmits the signal to the computing and controlling unit. If, simultaneously, the detector 108 does not detect the presence of a cell on the transfer disk 1 after the disk has advanced one step forward, the loading push-rod 110 is driven into alternative motion and pushes cell 3 into corresponding radial recess 2.

As said before, each cell is marked on the outside facing side with a bar-code. The transfer disk 1 moves the cell 3 stepwise to the bar-code read probe located between two successive angular stop positions of the recess 2 of the transfer disk 1. During this move, the cell 3 travels under blade 12 and the roller which tightly press the cell 3 into its recess 2. When it passes before the read detector 14, the computing and controlling unit identifies the type of analysis to be performed on the analytical sample. This information recorded on the cell requires that the user select a cell whose reservoirs 3a are already filled with one or more reagents suitable for testing that particular analytical sample. With this initial information, and taking into account that the computing and control units have memorized the angular setting of this cell relative to the initializing reference mark on disk 1, each further station will receive specific instructions on the operation to be performed therein.

It should be remembered here that the cell comprises two reaction cuvettes, one of which is for the analytical sample, the other one is for a comparison blank to be used eventually in the measurements.

The cell 3 which has just been set on the transfer disk 1, is not initially provided with a suspension of solid magnetic phase in reservoir 44, so pipet 24 coupled to jig 18 is not actuated. This cell 3 goes therefore to the second jig 19. Then, the movable tubular part 29, bound to the ball-bearing 3 is lowered by rod 32 driven by the journal 33 fastened to disk 34 fixed to the shaft of motor 35. This displacement of the tubular part 29 leads to the displacement of the jig's arm 19 and the hollow dropper point 21. During this move, the point pierces through a protective cap (not represented) on the side reservoir 3a located under said point 21 and the latter penetrates into it below the level of the reagent for instance the immunopartner to the analyte in this reservoir. The measuring piston of pipet 25 connected to the hollow point by flexible hose 23 is displaced through an unrepresented mechanism in a stroke corresponding to the volume of liquid desired. The rod 32 then lifts the tubular part 29 which is thereafter driven angularly by disk 38 in mesh with arm 36 by means of pin 37. When the hollow point is above one of the reaction compartments 3b of the cell, rod 33 again lowers the tubular part 29 to bring this hollow point 21 into the reaction compartment. The measuring piston of pipet 25 moves backwards in a stroke corresponding to the amount of reagent desired. The tubular part 29 is again lifted by rod 32 then it is angularly displaced by disk 38 in gear with arm 36 for putting the jig's arm in facing relation with the other reaction compartments 3b of cell 3. The hollow point is again lowered to dispense the same dose of reagent as in the neighboring compartment. Finally the jig 19 returns to its starting position, opposite to reservoir 3a in which the doses of reagents dispensed into reaction compartments 3b have been pumped and the hollow point can discharge therein the unused portion of reagent sampled initially. Then the jig 19 is once more lifted to remove the hollow point 21 from this reservoir.

The full reagent delivery cycles achieved in the 15 sec interval which seperates two consecutive displacement steps of the transfer disk 1. If, depending on the type of analysis to be effected, the second reservoir 3a of cell 3 contains a second reagent, the latter is distributed into both compartments 3b according to the same foregoing operation.

Then, transfer disk 1 continues its stepwise rotation. Naturally, the other cells which lie on the transfer disk 1 each receive a treatment in function to the analysis to be carried out therein, so each work station receives appropriate instructions relative to that cell which is positioned facing it.

When the one or more reagents have been introduced into the cuvettes, the incubation period is started. As said before, thermostatting of the medium in the cuvette is achieved by contacting the walls thereof with that of the radial recess 2, the disk 1 being heated to the desired temperature by heating resistor R embebbed therein.

In this Example the period of revolution is 7.5 min. (30 radial recesses=30 steps of 15 sec each) to which one must add the time of a partial revolution depending on the position at which the liquid phase is removed from the cell after separation of the solid phase. The incubation periods are therefore an integer multiple of 7.5 min. Thus, depending on the kind of analyses, the computing and control unit decides on the number of revolutions of each cell to complete the incubation of the cell content.

Then, during a next turn or a further one, when the cell 3 becomes positioned in front of the first pipetting station 16, the arm of jig 18 sucks a portion of solid phase (which comprises here a suspension of magnetic particles carrying a binder, i.e. a non-specific antibody of the reagent used for analyses) from reservoir 44. Actuation of jig 18 is in all respects identical with that of jig 19 described before and will not be repeated now.

When pipet 24 has sucked a given volume of this suspension in the hollow point 20, the jig brings this hollow point into, successively, each compartment 3b for adding a dose of the solid phase suspension to the liquid analyte. The cell is then displaced stepwise to the first mixing station 77 which follows the first washing station 46, after which a new incubation period is started.

During a next revolution of the transfer disk 1, the apparatus performs the magnetic separation of the solid phase before the washing step. For this, the washing station 46 is coupled with and preceded by the four permanent magnets 48 mounted on four respective rocking bases 49. These rocking bases are brought into an upper position by respective push-rod 52 which movably connects the bases 49 and the movable armature 53 of the electromagnet 54; in this position the permanent magnet 48 rests against the side wall of cell 3 and attracts the magnetic particles of the solid phase against the internal face of this side wall. As the displacement of the cell 3 by the transfer disk before the permanent magnets 48 progresses, the latter rest against the side wall of cuvette 3 and the magnetic particles are subjected for 45 sec to the influence of the magnetic field which causes them to migrate through the liquid to the internal face of this wall before they reach the washing station 46.

When cell 3 reaches this washing station 46, the fourth permanent magnet 48 rests against it and thus immobilizes the magnetic particles. The slide-rod 59 is displaced downwards by the rod 69 connecting this slide-rod to the driving disk 70 of the step-by-step motor 68, and the two pairs of hoses 60a, 60b, 61a, 61b are introduced into the two respective compartments 3b of cell 3.

Since the seat of the spout 63 is normally closed by the valve 64, the suction source 62 draws the liquid from each compartment 3b through hoses 60a, and 61a respectively. Then the push-rod 66 actuated by the electromagnet 67 lifts the valve 64 which interrupts the effect of aspiration.

Meanwhile, the piston of pump 71 was performing its aspiration stroke for admitting therein, the washing liquid. As soon as spout 65 opens by opening valve 64, the piston of pump 71 accomplishes its delivery stroke and introduces a dose of rinsing liquid into reaction compartments 3b by means of hoses 60b, 61b, respectively.

Then this cycle comprising a sucking step and delivery of washing liquid is further repeated twice, after which the slide-rod 59 is lifted up to withdraw the hose 60a, 60b, 61a, 61b from the reaction compartments 3b of the cell.

The cell 3 is brought in the next step in front of the mixing station 77 which imparts a fast rocking movement to the cell around the upper internal edge of the radial opening 2, by means of the rod 78 actuated by electromagnet 78 and return spring 80. The magnetic particles of the solid phase are therefore redispersed in the washing liquid.

After this redispersion stage, the cell is subjected to a second washing operation preceded by three successive magnetic separation steps. The only difference between this second washing stage and the afore mentioned first one is that after the liquid in the reaction compartments has been removed by suction for the third time, no further washing or rinsing liquid is reintroduced into these compartments and the cell leaves the washing station with only the solid phase and the complexes formed from the specific antigens possibly present in the biological analyte to be tested and also these in known quantity from the control sample in the second reaction compartment 3b. when cell 3 reaches the next reagent delivery pipetting station 82, the slide-rod 86 is lowered by the synchronous motor 99 and the rod 100 for bringing the hollow points 87, 88 into the respective reaction cuvette 3b. The peristaltic pump 91 then introduces into each cuvette 3b the same amount of liquid substrate by means of flexible hoses 89 and 90. This liquid substrate comprises sustances of which at least one will provide absorbance at one or more given wavelengths in the presence of the enzyme signal generator bound to the complexes immobilized on the magnetic particles of the solid phase.

Thereafter, the slide-rod 86 is returned in the upper position by motor 99 and rod 100 and the cell is driven to the second mixing station, identical with the first one; here the solid phase particles are again suspended in the liquid substrate. Then, a new variable period of incubation is started. As explained before, this period is an integral multiple of 7.5 min which corresponds to one revolution of the transfer disk 1 plus a fraction of revolution.

Once the incubation is over and when the cell again faces the piper delivery station 83, which is fully identical to the corresponding station 82, a quantity of liquid for stopping the reaction with the substrate is introduced by the peristaltic pump associated with this delivery station into each reaction compartment 3b of the cell.

When the content of the compartments of this cell 3 which reaches the measuring station 115 is to be measured, the slide-rod 120 actuated by rod 125 lowers the arm 119 which brings the end of duct 117 into one of the two compartments of cell 3, the free end of this arm being guided in groove 123, once the liquid from this cuvette of cell 3 has been transferred to photometer 118, rod 125 lifts back slide-rod 120 and arm 119. When the free end of side branch 119 reaches the top of groove 123 (FIG. 11), the electro-magnet 132 moves the rod 130 against the force of return spring 133, so this rod 130, causes arm 199 to swivel and bring the end of branch 119a to the top of groove 124. When rod 125 again lowers the slide rod 120, the arm is guided by branch 125a engaging in groove 124, so that the free end of the flexible pipe 117 is brought into the second compartment of cell 3, and this enables the transfer, to the photometer 118, of the liquid to be analyzed of this second compartment.

In the case when the photometer is not incorporated in the apparatus described, but is a separate unit, the cell is directed by arm 102 to the discharge ramp 104 wherefrom it can be taken and measured in this separate photometer.

We claim:

1. A method of measuring analyte antigens or antibodies in a biological fluid in appropriately designed reaction cells in an automated analytical apparatus, wherein said automated analytical apparatus comprises a closed circuit transfer path having means for transferring cells in a regular, step-by-step manner therealong, the step-by-step transfer of a cell around the entire transfer path defining a single revolution of the transfer means and being of predetermined duration, wherein a thermostating period for each analysis performed with the automated analytical apparatus is at least an integer multiple of said predetermined duration;

and a means for detecting a label reagent bound to said analyte antigens or antibodies;

said transfer path comprising a loading station, at least one reagent delivery station, at least one mixing and washing station, a separating station and a discharging station, each said station being provided for selectively operating on each said cell;

which method comprises the steps of:

placing a specific code on each said cell for identifying a kind of analysis to be effected with respect to that cell;

loading each said cell, in turn, to said transfer means at said loading station;

depositing into each said cell said biological fluid;

reading, with a code reading means, the code on each said cell;

transferring said cells in a regular, step-by-step manner along said closed circuit transfer path to at least one reagent delivery station, at least one mixing and washing station, a separating station and a discharging station;

adding to said biological fluid in each cell magnetic particulate carriers having antibodies or antigens immobilized thereon that are specific for said analyte antigens or antibodies;

controlling operations of said stations on each said cell based upon the analysis indentified by the respective code of each said cell, read by the code reading means;

controlling a temperature within each said cell around the entire transfer path;

retaining each said cell on said transfer means for a respective predetermined thermostating period by retaining said respective cell on said transfer means at least for a predetermined number of revolutions;

adding a label reagent to each cell, wherein said label reagent specifically binds to any analyte antigens or antibodies bound to the magnetic particulate carriers;

removing excess label reagent from each cell;

detecting the presence or absence of label reagent bound to said magnetic particulate carriers via said means of detection to indicate the presence or absence of said analyte antigens or antibodies.

2. Method according to claim 1 wherein said loading station is associated with two cell positioning photodetectors, one of them upstream of a loading ramp which opens vis-a-vis said transfer path and the other one within a ramp in facing relation with the position of the cell before the loading thereof.

3. Method according to claim 1, wherein said transfer means comprises a disk of a thermally conductive material embedded with heating elements and provided with recesses for housing said cells, wherein each of the holding recesses of the transfer means opens radially on the edge of said disk, each cell is positioned in its recess so that it partly extends above the upper face of the disk, and wherein said mixing and washing station comprises on one hand an elastic component which rests against the edge of the disk, and on the other hand, a rod mounted to slide back and forth radially with respect to the disk and above the upper face thereof with its front end adjacent to said cells, and an actuating electromagnetic part for driving this rod into longitudinal oscillating motion with a frequency sufficient to bring the cell's content into agitation.

4. Method according to claim 1, wherein the loading station and each mixing station are followed by pressure mechanisms which force the cell to stay in contact with a respective housing recess.

5. Method according to claim 1, wherein said transfer means is provided with housing recesses each having a shape closely corresponding to a shape of a portion of a cell, walls of the recesses being heated by said thermostatting means.

6. Method according to claim 1, wherein said automated analytical apparatus further comprises pipet delivery station, one of said pipet delivery station being in connection with a photometer.

7. Method according to claim 1, wherein the station adapted for carrying out step of reagent delivery comprises a reservoir containing a suspension of magnetic particles carrying an immobilized antibody or antigen, oscillating driving means connected to said reservoir the bottom of which comprises two ramps inclined in two opposite directions for providing a stirring action as a consequence of the intermittent oscillations of said reservoir.

8. A method as in claim 1, wherein said separating station comprises at least one magnetic separation station, each said magnetic separation station comprising a permanent magnet coupled to an actuating component capable of moving the magnet back and forth between two boundary positions, in one of which the magnetic field crosses the walls of said cell and in the other of which the magnetic field is remote from said walls and wherein the method further comprises selectively moving the magnet into said one boundary position when a said cell is at said separation station thereby to selectively achieve a magnetic separation.

9. A method as in claim 1, wherein said step of controlling the temperature comprises providing a transfer means including a disk of a thermally conductive material and having heating elements embedded therein and provided with recesses for housing said cells.

* * * * *

UNITED STATES PATENT AND TRADEMARK OFFICE
CERTIFICATE OF CORRECTION

PATENT NO. : 5,698,450
DATED : December 16, 1997
INVENTOR(S) : Ringrose et al.

It is certified that error appears in the above-identified patent and that said Letters Patent is hereby corrected as shown below:

On the title page, item [63] should read

Continuation of Ser. No. 264,756, Jun. 23, 1994, abandoned, which is a continuation of Ser. No. 978,478, Nov. 18, 1992, abandoned, which is a division of Ser. No. 238,922, Aug. 15, 1988, abandoned, filed as PCT/EP87/00603, Oct 10, 1987.--

Signed and Sealed this

Fifteenth Day of September, 1998

Attest:

BRUCE LEHMAN

*Attesting Officer*   *Commissioner of Patents and Trademarks*